United States Patent
Salzmann et al.

(10) Patent No.: US 6,365,405 B1
(45) Date of Patent: Apr. 2, 2002

(54) COMPOSITIONS OF CHONDROCYTES, PREPARATION AND UTILIZATION

(75) Inventors: Jean-Loup Salzmann, Paris; Andrès Crespo, Ormesson sur Marne; David Klatzmann, Paris; Norbert Passuti, Saint Sebastien sur Loire, all of (FR)

(73) Assignee: Universite Pierre et Marie Curie (Paris IV), Paris, Cedex (FR)

( * ) Notice: Subject to any disclaimer, the term of this patent is extended or adjusted under 35 U.S.C. 154(b) by 0 days.

(21) Appl. No.: 09/662,469

(22) Filed: Sep. 15, 2000

(30) Foreign Application Priority Data

Sep. 16, 1999 (FR) .............................. 99 11564

(51) Int. Cl.[7] .............................. C12N 5/08; C12N 5/02
(52) U.S. Cl. ........................ 435/366; 435/380; 435/381
(58) Field of Search ................................ 435/380, 381, 435/366

(56) References Cited

U.S. PATENT DOCUMENTS

| | | | | |
|---|---|---|---|---|
| 4,642,120 A | * | 2/1987 | Nevo et al. | 623/16 |
| 5,478,739 A | * | 12/1995 | Slivka et al. | 435/240.23 |
| 5,842,477 A | * | 12/1998 | Naughton et al. | 128/898 |
| 5,993,810 A | * | 11/1999 | Lebovitz | 424/94.67 |
| 6,001,352 A | * | 12/1999 | Boyan et al. | 424/93.7 |
| 6,017,747 A | * | 1/2000 | Craik et al. | 435/252.3 |

FOREIGN PATENT DOCUMENTS

| | | |
|---|---|---|
| EP | 0 430 635 A | 6/1991 |
| WO | 95 30742 A | 11/1995 |
| WO | 97 33975 A | 9/1997 |
| WO | 98 04681 A | 2/1998 |

OTHER PUBLICATIONS

Nixon et al: "Isolation, Propagation, and cryopreservation of equine articular chondrocytes" American Journal of Veterinary Research, vol. 53, No. 12, Dec. 1992, pp. 2364–2370, XP002129461 ISSN: 0002–9645, p. 2364–p. 2365.

Van Steensel M A M et al: "Optimization of cryopreservative procedures for human articular cartilage chondrocytes." Archives of Orthopaedic and Trauma Surgery, vol. 113, No. 6, 1994, pp. 318–321, XP000925592, ISSN: 0936–8051 *p. 318–p. 319.

Bujia J et al: "Culture and Cryopreservation of Chondrocytes from Human Cartilage Relevance for Cartilage Allografting in Otolaryngology" ORL (Otorhino–Laryngology) (Basel), vol. 54, No. 2, 1992, pp. 80–84, XP0009255590, ISSN: 0301–1569, *p. 80–p. 81 *p. 82–p. 84*.

Tomford W W et al: Studies on Cryopreservation of Articular Cartilage Chondrocytes Journal of Bone and Joint Surgery American Volume, vol. 66, No. 2, 1984, pp. 253–259, XP000929309, ISSN: 0021–9355, *p. 253–p. 254*.

Schachar N et al: "Cryopreserved Articular Chondrocytes Grow in Culture Maintain Cartilage Phenotype and Synthesize Components" Journal of Orthopaedic Research, vol. 7, No. 3, 1989, pp. 344–351, XP000925589, ISSN:0736–0266 *le doecument en entier*.

Shortkroff S et al: "Healing of chondral and osteochondral defects in a canine model: the role of cultured chondrocytes in regeneration of articular cartridge" Biomaterials, GB, Elsevier Science Publishers BV., Barking, col. 17, No. 2, 1996, pp. 147–154, XP004032812, ISSN:0142–9612 *le document en entier*.

Paige K T et al: Injectable cartilage Plastic and Reconstructive Surgery, US, Williams and Wilkens Co., Baltimore, MD, vol. 96, no, No. 6, Nov. 1995, pp. 1390–1398, XP002101649, ISSN: 0032–1052 *le document en entier*.

Loredo G A et al: "Influence of alginate polysaccharide composition and culture conditions on chondrocytes in three–dimensional culture" Tissue Engineering, US, Larchmont, NY, vol. 2, No. 2, 1996, pp. 115–125, XP002101650, ISSN: 1076–3279 *le document en entier*.

* cited by examiner

Primary Examiner—James Ketter

(57) ABSTRACT

This invention concerns compositions of chondrocytic cells, notably human ones, and the methods for preparing and using them. More specifically, the invention describes the production of autologous human chondrocyte suspensions, employing recombinant enzymes and/or media that are compatible with pharmaceutical use. The invention also describes methods and compositions for freezing chondrocytes, notably in the absence of DMSO. The chondrocytes which are produced can be used in vivo to restore affected cartilaginous structures, such as in post-traumatic cartilaginous defects or dissecting osteochondrite of the knee or, more generally, for treating and repairing clinically significant defects in cartilage, notably in joint cartilage.

19 Claims, No Drawings

COMPOSITIONS OF CHONDROCYTES, PREPARATION AND UTILIZATION

This invention concerns compositions of chondrocytic cells, particularly of human origin, and methods for preparing them. It also concerns the use of these compositions to implant chondrocytes in vivo, to treat various pathologies. More particularly, the invention describes the production of suspensions of autologous human chondrocytes, techniques for conserving them, and their use in vivo to restore cartilaginous structures affected, such as post-traumatic cartilaginous defects or the dissecting osteochondritis of the knee, or, more generally, to treat and repair clinically significant defects in cartilage, particularly in articular cartilage.

Chondral lesions, such as, for example, focal lesions of the knee's articular cartilage, in the load bearing zone, greatly expose the subjects to osteoarthritis. This type of lesion is frequent (from trauma, sports activity, dissecting osteochondritis, etc.) and produces a significant gene. The capacity for spontaneous repair of chondral lesions is modest. They can be characterized by the presence of fibrocartilaginous scars, through arthroscopic studies. Essentially these lesions are treated by washing, which temporarily heals the symptoms, but does not treat the origin of the defect and, in particular does not prevent progressive degradation of the cartilage. This osteoarthritic evolution of the cartilage in reality, it appears, can be treated effectively only by replacing the defective cartilage with healthy cartilage. In particular, the use of cells other than chondrocytes results in ineffective repair to the cartilage, because it changes the nature of the extracellular matrix.

This is why the literature describes the production and therapeutic use of human chondrocytes, specially the autologous ones, to reconstitute or compensate for defects in cartilage.

Thus, isolation of chondrocytes is practiced, starting from various types of cartilage or even from precursors drawn from bone marrow. For this purpose, a sample of healthy cartilage (or marrow) can be taken from a subject, mechanically dissected to form fragments of reduced size, then treated in the presence of one or several enzymes, generally trypsin and/or an extracted collagenase, in order to separate the chondrocytes contained in the cartilage. The chondrocytes can then be cultivated, generally in a monolayer, to obtain a sufficient number of cells (several passages generally are performed.) Although chondrocytes dedifferentiate in the form of fibroblasts during their culture and expansion phases, it has been shown that the chondrogenic cells obtained could differentiate themselves again into functional chondrogenic cells, either in situ or in vitro, through insemination in three-dimensional cultures.

Various approaches have been developed to grow in vitro chondrocyte cultures, and various treatment strategies have been developed. In particular, international application number WO95/30742 proposes reconstituting artificial cartilage patches in vitro (that is, multilayer chondrocytes included in an endogenous extracellular matrix) of a predefined form and volume, and to implant these patches onto the site being treated. Other strategies are based on producing chondrocyte cultures (or chondrocyte cells) in vitro expanded, which are implanted directly to reconstitute the cartilage in situ, or after biocompatible synthetic matrices have been deposited. The use of factors that stimulate the growth of precursors to chondrocyte cells has also been suggested, in order to induce chondrocyte production in situ.

This invention presently describes new compositions and methods enabling the conditions of production and utilization of chondrocytes to be improved, for therapeutic applications. This invention describes, in particular, new methods which result in improved production of chondrocytes. Notably, this invention describes chondrocyte production techniques which enable pharmaceutical quality chondrocyte preparations to be generated. This invention also describes new techniques which allow chondrocytes to be conserved efficiently, notably in frozen form, which considerably promotes the conditions for implementing a clinical grafting program. This invention can be implemented to generate suspensions of autologous human chondrocytes which are intended to be implanted in vivo, or to be used in producing artificial cartilage patches, or also to be used in preparing synthetic matrices covered with chondrocytes. This invention also describes methods for implanting chondrocytes in the areas to be treated (notably, cartilage).

Thus, a first aspect of the invention resides in the production of chondrocytes from a biological sample, in particular of chondrocyte cultures from a biological sample comprising chondrocytes included in an cartilaginous extracellular matrix, and even more preferably of chondrocytes suspensions from a biopsy of cartilaginous tissue. The invention's processes include various stages of treatment and conditioning of the biological sample, then of chondrocyte culture and treatment, making it possible to obtain preparations of chondrocytes of pharmaceutical quality, that is, which can be used in human therapy.

To enable this invention to be more clearly understood, the following definitions are provided:

Cartilage (or cartilaginous tissue): The cartilage is essentially formed of chondrocytes, incorporated into an extracellular matrix. The extracellular matrix mainly includes collagen (essentially of type II) and proteoglucanes (essentially, proteins to which are connected glucosamine glucanes such as chondroitin sulfate and keratane sulfate). The extracellular matrix is serrated by the chondrocytes. There exist various types of cartilage, such as hyalin cartilage (notably present in joints, in particular the rib, nasal, bronchial cartilage, etc.), the elastic cartilage, which in addition encloses the elastin fibers (present, for example, in the ear) and the fibrous cartilage, which moreover encloses Type I collagen (present, notably, in intervertebral disks, the meniscus, etc.). In terms of the invention, cartilage designates all types of cartilage, notably including chondrocytes and an extracellular matrix.

Chondrocytes are cartilage cells which secrete the extracellular matrix. In terms of this invention, the term chondrocyte designates more specifically the cells which secrete the cartilaginous extracellular matrix, notably type II collagen and proteoglycanes such as "agrecannes". In terms of this invention, the term chondrocyte also includes "chondrogenic" cells, that is, cells which are capable of producing chondrocytes. Thus, this consists of cells that are apt of producing the cartilaginous extracellular matrix, such as chondrocyte precursors, notably mesenchymatous precursors (or mesenchymatous stem cells), or dedifferentiated chondrocytes, for example, following cultures in monolayers. The term chondrocyte also designates primary cultures (freshly isolated from biopsies) as well as cells expanded in vitro, including genetically modified, immortalized, selected, conserved, etc.

According to a primary advantageous characteristic, the invention provides that the production method includes a stage of a) treatment of the biological sample in the presence of a recombinant enzyme, thus facilitating the dissociation of chondrocytes, in particular through hydrolysis (at least partial) of collagen molecules contained in the sample.

As it will be explained in detail further on, a primary characteristic of the invention's process consists of the employment of a recombinant enzyme to dissociate the biological sample, notably, the cartilage biopsy. In effect, this invention shows that the use of such an enzyme improves not only the quality of the product, but also the effectiveness of the process.

Thus, the objective of the invention is to develop a process for dissociation chondrocytes contained within a biological sample, including the in vitro treatment of this biological sample in the presence of a recombinant enzyme capable of hydrolyzing collagen molecules, particularly those of a recombinant collagenase.

Another object of the invention is to utilize a recombinant enzyme that is capable of hydrolyzing collagen molecules, particularly those of a recombinant collagenase, to dissociate human chondrocytes in vitro.

In the invention's process, chondrocytes are thus dissociated from the biological sample and, in a stage b), are cultivated in a monolayer t o make them multiply (or expand), or are directly inseminated within a gel, with the aim of making them multiply. In the case of monolayer cultures, the chondrocytes adhere to the material surface of the culture medium being used. Upon completion of the culture, the cells thus are detached for harvesting and then, if applicable, are placed into suspension. In the invention's process, the cells can be detached by any technique known to practitioners (in particular, a treatment with trypsin). However, according to another advantageous characteristic of the invention's process, chondrocytes are detached by treating the cells in the presence of a solution containing at least one compound chosen from among the polyosidic compounds. In effect, a second aspect of this invention also consists of evidencing that chondrocytes can be detached effectively from t heir supporting structure, without affecting their functional properties, by placing them in contact with a medium containing particular compounds chosen from among the polyosidic derivatives. The use of this type of compound may be seen to be particularly advantageous for therapeutic applications, to the extent these compounds do not present a recognized pathogenicity or are, in the case of a few among them, already being used as pharmaceutical products.

Thus, another aspect of the invention concerns a process to detach chondrocytes that adhere to an in vitro culture, comprising placing chondrocytes in contact with a medium comprising at least one compound chosen from among the polyosidic derivatives (notably, heparin).

The object of the invention is also to utilize a compound chosen from among the polyosidic derivatives, heparin in particular, to detach chondrocytes in culture.

Thus, in a more specific embodiment, according to the invention, the production process to prepare chondrocytes comprises:

a) treatment of a biologic sample in the presence of a recombinant enzyme, permitting dissociation of chondrocytes, b) culturing, in a monolayer, chondrocytes thus dissociated, and c) placing the chondrocytes in contact with a medium containing at least one compound, chosen from among the polyosidic derivatives, in order to detach the adhering chondrocytes.

In another variant of the invention, the method of producing a chondrocyte preparation comprises:

a) treatment of a biological sample in the presence of an enzyme which permits the chondrocytes to be dissociated, b) the culture in a monolayer of the chondrocytes thus dissociated, and c) placing the chondrocytes in contact with a medium containing at least one compound chosen from among the polyosidic derivatives, in order to detach adhering chondrocytes.

In the invention's process, stages b) and c), described above, can be repeated several times so as to generate a significant number of chondrocyte cells, from the biological sample, with each cycle that is repeated being commonly designated by the term "passage". The repetition of stages b) and c), and the resulting expansion of chondrocytes, are especially significant for autologous grafting applications, where it is essential to produce a sufficient quantity of chondrocytes, starting from a biopsy, in order to relieve the patient's cartilaginous defect.

Once the cells have been detached from the support structure, they are then recovered by means of all appropriate devices (phial, tube, flask, pocket, etc.). Generally, the cell's density is determined in order to evaluate the number of available cells. Cellular viability and sterility are also tested to verify the quality of the preparation obtained.

Thus, according to the invention, in a particular embodiment, the production process employed in preparing chondrocytes comprises:

a) treating the biological sample in the presence of a recombinant enzyme enabling chondrocytes to be dissociated, b) culturing in a monolayer the chondrocytes that are thus dissociated, c) placing the chondrocytes into contact with a medium containing at least one compound, chosen from among the polyosidic derivatives, in order to detach the adhering chondrocytes, d) if applicable, repeating stages b) and c) once or several times, and e) recovering the cells that have been produced.

In another embodiment of the invention, the production process to prepare chondrocytes comprises:

a) treating the biological sample in the presence of an enzyme, enabling the chondrocytes to be dissociated, b) culturing in a monolayer the chondrocytes that are thus dissociated, c) placing the chondrocytes into contact with a medium containing at least one compound, chose from among the polyosidic derivatives, in order to detach the adhering chondrocytes, d) if applicable, repeating stages b) and c) once or several times, and e) recovering the cells that have been produced.

The cells thus produced can be placed in suspension in all desired media, and be utilized as a therapeutic product. In fact, the literature has reported the implantation of chondrocytes in suspension, notably autologous ones, for clinical applications to regenerate cartilaginous tissue. These cells can also be utilized in applications including research and study of the development and biology of chondrocytes, to produce banks of nucleic acids derived from chondrocytes, etc. These cells can also be manipulated, for example, to introduce heterologous nucleic acids. Finally, the cells can be seeded in three-dimensional cultures or in non-adherent supports, to form in vitro matrices to be implanted, or artificial cartilage.

In this regard, to facilitate all of this manipulation, and for all other later use, these cells can also be conditioned, notably through freezing. For this purpose, this invention also describes particularly effective compositions and methods to conserve chondrocytes, notably in frozen form. These methods enable the chondrocytes to be conserved for long periods without affecting their functional properties. In addition, the compositions and methods employed can be compatible with therapeutic use, and thus permit preservation of chondrocytes, or compositions of chondrocytes, which are to implanted in vivo. Thus, in a particular mode of implementation, the process of invention further comprises an f) stage comprising freezing the chondrocytes thus obtained.

Freezing can be accomplished under varying conditions and in the presence of various agents or protective compounds. Thus, according to a first variant of the implementation process, freezing is performed in the presence of dimethyl sulfur oxide ("DMSO"). DMSO is a well-known protective agent which is inserted into cellular membranes and enables them to be stabilized, which prevents cells from being destroyed. According to the invention, this type of freezing medium can be implemented with chondrocytes.

In a particularly advantageous manner, freezing is performed in the absence of DMSO. More particularly, this invention presently describes methods and compositions to freeze chondrocytes or other eucaryotic cells, under conditions which are compatible with direct therapeutic use (i.e., without treating defrosted compositions).

The invention concerns, notably, all medias which enable chondrocytes to be frozen, deprived of DMSO and/or glycerol, and which are compatible with therapeutic use (that is, they can be administered to a subject without a prior washing or centrifuging stage, for example). More particularly, this concerns a composition containing at least:

human albumin a modified gelatine or a polysaccharide, and possibly a saline solution.

In this respect, the invention more particularly describes the implementation of new media for conserving eucaryotic cells, comprising:

human albumin a polysaccharide possibly a saline solution.

In effect, this invention shows that such mediua can be utilized to preserve eucaryotic cells, and to freeze them without substantially affecting their viability. Thus, the invention shows that, in adapting the respective proportions of the constituent parts and the number of cells, these media can be used to freeze eucaryotic cells, without incurring a significant reduction in the cells when they are frozen, particularly with a reduction of less than 35% of viability, and, preferably, less than 25%, and yet more preferably, less than 15%.

In these conservation media, the polysaccharide employed can be of variable structure and molecular weight. Preferably, it consists of a sulfated polysaccharide, preferably with a molecular weight ranging between 5,000 and 500,000 daltons, and preferably between 30,000 and 250,000 daltons. The polysaccharide can be chosen, for example, from dextran (40,000 or 60,000 daltons), starch, hydroxyethyl-starch (240,000 dalton), etc.

The saline solution can consist of any isotonic solution described in the text, below.

Human albumin can be from extracted albumin or recombinant albumin, obtained according to techniques familiar to practitioners, as described in detail in the text, below.

Specifically, one may cite, as a medium according to the invention, those media which contain human albumin and a composition of plasma substitute, such as Hemodex$^R$, Hesteril, Plasmaclair$^R$ or yet Rheomacropdex. These products are used in the clinic and are reported in Vidal.

According to the invention, in these media the respective quantities of constituent parts can vary, according to the cell type employed, the nature of the polysaccharide, etc. Generally, the media cited in the invention contain from 5% to 45% of a solution of human albumin at 20%, and 95% to 55% of polysaccharide, possibly in a saline solution.

According to the invention, these media, based on polysaccharide and albumin, and deprived of DMSO (and, preferably, of glycerol), can be utilized in conserving and/or freezing various types of eucaryotic cells, such as mammal cells, notably human cells. These may consist of primary cultures, cell lines, genetically modified cells, virus-producing cells, etc. By way of illustration, one may cite blood cells (erythrocytes, granulocytes, lymphocytes, dendritic cells, macrophages, etc.), embryonic or somatic stem cells, endothelial, muscular, hepatic, nerve, fibroblastic, chondrocyte cells, cells used in producing retrovirus, cells modified to produce therapeutic compounds, etc. In a particular mode, according to the invention, the medium is implemented to conserve antigen-presenting cells, notably monocytes, macrophages, dendritic cells or their derivatives. In addition, the invention's medium can be implemented to conserve concentrated blood or erythrocytes, which are currently stored in the presence of DMSO or glycerol.

Moreover, this invention describes effective methods for adapting the composition of such media, that is, to improve their effectiveness, as shall be described in detail, below.

In a particular method of implementing the invention, chondrocytes are frozen in a medium containing a saline solution, human albumin and a gelatine derivative (in particular, a modified gelatine) or a polysaccharide.

A more particular object of the invention consists also of a method for freezing chondrocytes, notably human chondrocytes, involving placing a chondrocyte preparation, human chondrocytes in particular, in contact with a medium containing a saline solution, human albumin and a gelatine derivative or a polysaccharide, preferably a polysaccharide, and freezing the resulting composition. More preferably, in the invention's cryopreservation method, the preparation of chondrocytes, specifically of human chondrocytes, comprises at least approximately $5 \times 10^6$ cells/ml, and more advantageously, at least around $10^7$ cells/ml.

Another particular object of the invention also resides in a composition comprising chondrocytes, notably human chondrocytes, a saline solution, human albumin and a gelatine derivative or a polysaccharide, preferably a polysaccharide. Preferably, according to the invention, such compositions contain at least $5 \times 10^6$ chondrocytes/ml, and more advantageously, at least around $10^7$ chondrocytes/ml.

The invention also concerns all composition containing in vitro dedifferentiated human chondrocytes and a pharmaceutically acceptable vehicle.

Chondrocyte methods and preparations, according to the invention, following thawing, if applicable, can be utilized in vitro or in vivo, via implantation or injection. Further on in the text, a more detailed description of the stages of the invention's process will be presented.

Obtaining the biological sample

The biological sample utilized in implementing the invention may consist of any tissue sample that contains chondrocytes. It may consist of a fragment of cartilaginous tissue (hyalin, either elastic or fibrous), of marrow, or of all other biological matter containing chondrocytes (including chondrocyte precursors).

In a preferred method of implementing the invention, the biological sample is a fragment of cartilage, preferably a fragment of human cartilage, and even more preferably a fragment of healthy human cartilage, particularly of the autologous sort. Cartilage can be taken from various areas, notably from the articulating joint areas. In this regard, in a preferred embodiment, the biological sample is a fragment of joint cartilage. This type of cartilage can be taken from various areas, such as the femoral condyle, the incisura, etc. The sampling can be performed, more specifically, from the superior-external part of the femoral condyle, or else in the lateral external part of the incisura. Such samples make it easy to obtain sufficient quantities of primary chondrocytes in order to produce, according to the process described in the invention, preparations of human chondrocytes at a concentration of 20 to $30\times10^6$ cells/ml.

The biopsy is generally taken from a healthy area of the cartilage, via arthroscopy, so as to obtain a quantity that is greater than or equal to approximately 100 mg of cartilage, preferably at least 150 mg of cartilage. A typical sample includes no less than around 200 mg of cartilage. It is understood that the cartilage used in taking the biological sample is a healthy tissue, containing healthy chondrocytes. For this purpose, the donor subjects from which the samples are taken can be subjected to various serological tests, notably for viruses (HIV, HBC, HCV, Hepatitis, etc.). Generally, in the case of therapeutic uses (chondrocyte grafts), the following criteria for exclusion are applied: Pregnant women, persons who are blood positive for HIV or hepatitis, or with allergies to gentamicin, antecedents of total meniscectomy or of the rupture of one or more crossed ligaments, mirror lesions on the tibial plane, pathology of the patella (instability, chondropathy), frontal misalignment of the upper knee at 10°, or osteoarthritis.

To take a sample, one takes a core sample of the knee cartilage, through arthroscopy, from the upper-external area of the femoral condyle, while sampling the entire thickness of the cartilage. After taking a sample, the biological sample can be treated in various ways. In an initial implementation procedure, the biological sample is utilized directly in the invention's process for producing chondrocytes. With this objective, it can be placed, first of all, in a transport medium, in the case in which the sampling and treatment of the biological sample are performed in different places (for example, at the hospital for taking the sample and in a laboratory for the treatment and production of chondrocytes).

In a particular mode of implementation described by the invention, the biological sample is placed in a nutritive medium, at a low temperature (approximately 4° C.), to be conserved for later use. Under these conditions, it is possible to conserve the biological sample for several weeks. This mode of implementation is particularly advantageous because it eliminates the time constraints generally encountered in grafting processes that employ autologous chondrocytes. In this regard, the invention describes, and currently supports, the possibility of maintaining the biological sample for a given time period, prior to the chondrocyte production phase, without significantly altering the sample's properties, notably the viability of the chondrocytes it contains.

Thus, in a particular mode, the invention also concerns a process for producing a chondrocyte culture from a biological sample, including taking the biological sample and treating it to produce chondrocytes. The process is characterized in that this biological sample is conserved in a nutritive medium prior to the chondrocyte production phase.

More particularly, the biological sample is placed, during a period which may extend from 1 to 15 weeks, or possibly more, in a nutritive medium at a preferably low temperature (for example, between approximately 2 and 8° C., and, more preferably yet, on the order of around 4° C.).

In a particular mode, the invention's process described above is thus characterized in that the biological sample is maintained in culture, in a nutritive medium, prior to stage a).

The nutritive medium utilized in conserving the biological sample can be a culture medium adapted to cells or mammal tissues (DMEM, Eagle, RPMI, etc.). The medium can be supplemented by various agents, such as antibiotics, amino acids, minerals, vitamin C, etc., and by autologous serum or human AB serum that has been rendered safe (that is, taken in advance and tested for the presence of viral contaminants, with the donor subject being retested for the presence of such contaminants several months afterward). Moreover, the medium may include an enzyme capable of dissociating the cells and/or the extracellular matrix (in particular, of hydrolyzing the collagen), so as to initiate or realize the subsequent stage a) of the process in a manner that is compatible with said objective. And, preferably, it consists of a recombinant collagenase, as described below. In this regard, it may consist of a recombinant collagenase that is active at low temperature, for example, at 4° C. Such a collagenase can be prepared by directed mutagenesis according to techniques known to practitioners. The medium's final and precise composition can be adapted by the skilled person. Preferably, the biological sample is placed into a sac and is conserved at 4° C., in darkness, and possibly is slowly agitated.

Stage a): Treatment of biological sample

The biological sample is treated according to the process described by the invention, to dissociate the chondrocytes it contains. As indicated above, the first stage of the process includes enzymatic treatment of the biological sample, in order to disaggregate the sample and to recover the chondrocytes.

Prior to the enzymatic treatment, the biological sample can nonetheless be conditioned, for example, via mechanical treatment (cut up or dissected mechanically), in order to obtain a tissue-based preparation composed of small-scale fragments, notably on the order of 1 to 10 $mm^3$, preferably inferior to 5 $mm^3$. The homogeneity of this preparation is not critical. Nevertheless, it is preferable that the greater portion of the fragments obtained have a dimension of less than 10 $mm^3$, so as to increase the efficiency of the process. Said dissection of the sample can only be performed by known methods, such as, for example, with the aid of a set of pincers, scalpel, scissors, lancet, screen on grills, etc., all in sterile condition.

Thus, the procedure described by the invention includes a prior stage consisting of collecting the biological sample and then, if applicable, a stage calling for its mechanical dissection.

The biological sample is then subjected to a treatment in the presence of a composition comprising at least one recombinant enzyme capable of hydrolyzing the collagen, preferably Type II collagen, or, more generally, capable of degrading one or more constituent parts of the cartilaginous extracellular matrix (composed mainly of Type II collagen, associated with proteoglycans).

An enzyme that is preferred for this stage is collagenase. In this regard, it is known that several extracted bacterial collagenases can be used (that is, naturally purified) to dissociate the cartilage. This invention shows, nonetheless, that various types of recombinant collagenase can be employed, and that their use presents several advantages.

Thus, in a preferred method of applying the invention's process, in stage a), the biological sample is treated in the presence of a recombinant collagenase.

The term "recombinant" indicates that the collagenase has been produced in an artificial system, through the expression of a nucleic acid coding for this enzyme. More generally, it consists of a collagenase produced by a host cell in which a nucleic acid coding a collagenase (or a fragment or a functional derivative of the latter) has been introduced artificially, or by a cell descending from such a cell (by divisions and/or derivations). By comparison with the extracted enzyme, the recombinant enzyme thus generally presents the following characteristics:

a determinate structure determinate glycosylations the absence of unidentified contaminants or pathogens the absence of trypsin a known and homogenous composition.

The recombinant collagenase utilized is preferably of bacterial origin, such as, for example, collagenase A, collagenase P, collagenase of Vibrio Alginolycus (EP430646) or the ColH collagenase of Clostridium Histolycus (J. Bact. 181 (1999) 2816). Other collagenases can also be used, such as collagenases of eucaryotic origin, notably mammalian, and human for example. In particular, one may utilize various types of mammalian (recombinant) collagenases, which are specific to Type II collagen and/or to cartilage, or also modified collagenase, for example through directed mutagenesis, possessing improved properties in terms of efficiency, selectivity, conditions of activity, etc. In particular, it may consist of a modified collagenase (for example, through directed mutagenesis) capable of biological activity at low temperatures which are, notably, below 20° C., and, still more preferably, lower than 10° C.

The use of recombinant collagenase according to this invention offers numerous advantages by comparison with the previous techniques, based on the use of natural collagenases. The first advantage lies in the absence of contaminants which are capable of affecting the quality of the chondrocyte preparation. In effect, the recombinant collagenase according to the invention is produced advantageously under Good Manufacturing Practices (GMP) conditions, and thus essentially lack all biological contaminants that are incompatible with therapeutic use. The invention's process thus allows preparations of pharmaceutical quality chondrocytes to be supplied. In addition, another advantage of the use of recombinant collagenase lies in the superior efficacy of the recombinant enzyme when compared with the natural enzyme. Thus, the results obtained show that recombinant collagenase permits a more rapid dissociation and/or lower doses of the biological sample. This constitutes a valuable advantage of the process described by the invention, by comparison with procedures employing extracted collagenase.

These collagenases can be produced in all appropriate cell hosts, that is, in particular in all host cells which do not have a recognized pathogenic character. The dissociation stage is generally performed at a temperature near the temperature of the human body, for example, between 32 and 40° C., preferably near 37° C., for a period which the practitioner may vary as a function of the quantity of enzyme utilized (from 0.05 to 5 mg/ml, preferably from 0.1 to 1 approximately ml/ml).

A typical stage of dissociation, according to the invention, consists of placing the biological sample (which, as applicable, is treated mechanically as described above) into contact with recombinant collagenase (0.5 mg/ml) for about 15 hours at 37° C., under agitation.

For the dissociation stage, recombinant collagenase can, moreover, be utilized in combination with other enzymes, either recombinant or extracted, whose quality will have been controlled.

Moreover, as indicated before, the dissociation stage can be conducted in a nutritive culture medium in which the biological sample is conserved. Under these conditions, according to a particular method of implementing the invention, the biological sample which has been collected is placed into a nutritive medium (preferably at a low temperature, for example, between approximately 2 and 8° C.), comprising an enzyme capable of degrading one or several constituent parts of the cartilaginous extracellular matrix, for a period which can range from 1 to 15 weeks.

Stage b): Monolayer cultures

Chondrocytes thus dissociated from the biological sample are, in stage b), cultivated in a single layer to make them multiply (or expand).

Prior to the culture, the digestive medium (utilized in stage a) is eliminated by centrifugation, and the cells are washed several times in a fresh culture medium. The cultures can be performed in all culture media which are appropriate to proliferation of mammalian cells, notably human cells. Preferably, complete media are utilized in this stage, that is, culture media supplemented by fetal calf serum or by autologous serum or human AB serum that is rendered safe, and with antibiotics (for example, Gentamicin), vitamins (for example, ascorbic acid) and HEPES. Specific usable media include, for example, the HAM F12, DMEM and RPMI media, either alone or in combination(s), supplemented, if applicable. Specific media have been described in the literature, whether consisting of defined media, of media without serum, etc. (see, notably, Adolphe et. al., Exp. Cell. Res. 155 (1984) 527; Jennings et al., Cell Biol. Int. Reports 7 (1983) 149; WO98/04681, which are incorporated with these presents by reference). Typically, cells are inseminated to an initial concentration which is less that 10,000 cells/cm2, generally between 5,000 and 10,000 cells. Generally, the medium is replaced every 2 to 3 days by a fresh medium.

The monolayer culture can be implemented in various appropriate culture devices, such as dishes, flasks, sacs, rolling bottles, multi-tray devices, cell-cubes, cartridges, etc. In this regard, according to a particular variant of the invention, monolayer cultures are performed in portable isolators or in triangular sectional bottles, equipped with narrow channels or openings and culture chambers of various sizes. This type of device allows several passages to be made, advantageously, in sterile devices, while easily controlling the supply and replacements of culture media.

Monolayer cultures can be performed for varying durations. Generally, they are conducted until the cells approach confluence, from 1 to 4 weeks, more often from 2 to 4 weeks, generally on the order of 3 weeks.

Stage c): Detachment of cells

Chondrocytes in culture, notably in a monolayer culture, adhere to the support walls utilized for cultures. Thus, it is useful to detach them from the walls in order to harvest them.

Generally, chondrocytes are detached from the support structure when the culture approaches confluence. More precisely, the cells' detachment stage is realized when the culture reaches 60% to 95% of confluence, more preferably 60 to 90% of confluence. This stage can be evidenced by the skilled person through conventional techniques (through measurements of optic density, by visual examination, etc.). To implement this stage, the culture medium preferably is eliminated, then the cultures are incubated in a fresh medium containing the chosen component, or compounds (detachment medium). It is understood that compounds can be added directly into the cells' culture medium, even though this method is not preferred. The medium utilized for detachment may be of identical composition to that employed for the cells' monolayer culture. Clearly, it may also consist of all other media which are adapted to mammalian cell cultures, notably chondrocytes. Preferably, it consists of a buffered saline solution comprising the active compound or compounds (enzymes, chelators, etc.). In this case, once the compounds have acted (generally less than 10 minutes after their incubation with the cells), some quantity of complete culture medium is added in order to inhibit their action and to protect the cells. If necessary, the cellular single layer (range) can then be easily dissociated mechanically (pipette).

As indicated, according to an advantageous method of implementation specified by this invention, chondrocytes are detached through incubation, in the presence of an medium containing at least one compound chosen from among the polyosidic derivatives.

The polyosidic derivative can be of a different nature. More generally, it consists of a polyosidic polymer, either of natural or synthetic origin, but compatible with clinical usage. Advantageously, the polymer is a polysaccharide, notably a sulfated polysaccharide, preferably with a mean molecular weight ranging from 5,000 to 500,000 daltons, and, preferentially, between 5,000 and 100,000 daltons. The sulfated polysaccharide can be chosen preferably from heparin and dextran-sulfate, with a strong preference for heparin.

Heparin has a mean molecular weight of approximately 20,000 Da, and is utilized as an anti-coagulant medication, as are its derivatives of lower molecular weight. For example, heparin is sold, in lyophilized form, by the Choay company. To ensure good utilization according to the invention's process, the polyosidic derivative is preferably added to a concentration ranging from 30 to around 2000 units per ml, advantageously between about 50 and about 1000 Ul/ml, and even more preferably between approximately 100 and approximately 1000 U/ml. Moreover, the detachment medium can include, in addition to the polyosidic derivative, chelators such as EDTA, for example.

Stage d): Expansion of Chondrocytes

In the production process according to the invention, in order to multiply the quantity of chondrocytes, several passages can be accomplished in the monolayer culture.

As indicated previously, repetition of stages b) and c) of the process, and the resulting expansion of chondrocytes, are particularly important for applications of autologous grafts, in which it is essential to produce a sufficient quantity of chondrocytes, starting from a biopsy, to relieve the patients cartilaginous defect.

Generally, stages b) and c) can be repeated from one to ten times without reducing cellular viability. The performance of 10 passages usually allows a satisfying number of chondrocytes to be generated, for all therapeutic applications, from all biological samples. More often, the process according to the invention calls for 1 to 7 passages of cells, 3 for example. It is understood that the number of passages can be easily adapted by the practitioner as a function of the initial volume of the biological sample, or of actual needs, etc.

Recovery and conditioning of chondrocytes

Cells which are thus produced can be recovered and conditioned for multiple uses. In general, cells issuing from the same biological sample are collected and assembled, which permits compositions of autologous cells to be produced. First of all, these cells can be replaced in suspension in any desired medium and be used as they are, as a therapeutic product. In effect, implantation of chondrocyte suspensions, notably the autologous ones, for clinical applications in the regeneration of cartilaginous tissue, has been reported in the literature. In this regard, although chondrocytes generally are dedifferentiated during the course of several passages, it has been shown that chondrocyte suspensions could re-differentiate themselves in situ, following implantation. Thus, it is possible to prepare compositions comprising suspensions of chondrocytes obtained according to the aforementioned process, for example, from $10^5$ to $10^8$ chondrocytes per dose. In a particular embodiment, the chondrocytes are conditioned in a gelified medium, thus ensuring improved handling and enabling the implant to take more effectively.

With this objective, cells that are harvested can be washed several times in a fresh culture medium, then exposed to any physiological solutions (buffer, saline, etc.) that are adapted for therapeutic use, notably for administration in vivo. Typically, the cells can be exposed to a 4% albumin solution or in an autologous serum or in AB human serum that is subjected to measures to make it safe, in a volume that is selected to obtain the desired concentration of cells. For example, immersion of cells in a volume of 0.4 ml enables a concentration of autologous cells to be obtained in excess of $10^7$ cells/ml, for example. These cells can be placed in tubes, ampoules, syringes, etc., under sterile conditions, and can be utilized for injection.

The chondrocytes obtained (after one or several washings) can also be placed in culture in a gelified medium, so that they might expand and that their subsequent implantation can be performed more easily.

In another variant, the harvested chondrocytes (after one or several passages) can be reinserted into a culture, under certain conditions, so as to promote their re-differentiation. This allows in vitro production of chondrocytes which secrete an extracellular matrix (notably, of type II collagen and proteoglycanes). This new culture can be performed, for example, in a three-dimensional culture (for example, in the presence of a biocompatible matrix), or in non-adherent supports.

The three-dimensional culture, for example, using alginate beads or biocompatible fibers, has been described in the literature (Guo et al., Conn. Tiss. Res. 19 (1989) 277; U.S. Pat. No. 5,736,372; U.S. Pat. No. 5,041,138; U.S. Pat. No. 4,846,835; U.S. Pat. No. 4,642,120). These techniques allow the formation in vitro of matrices ready to be implanted in areas to be treated.

Culture in non-adherent supports has been described, for example, in application WO95/30742. This consists essentially of cultivating cells in the support medium whose surface has been rendered functional in order to prevent cellular adhesion. Thus, cells are capable of proliferating in suspension, to re-differentiate and to produce an extracellular, endogenous matrix in which they are embedded. This approach leads to constitution, in vitro, of artificial cartilages, in a predetermined volume and form, suitable for use in implantation.

The chondrocytes produced can also be manipulated, for example, for the purpose of introducing heterologous nucleic acids, in view of conferring additional properties to them.

Chondrocytes can also be utilized in vitro, in a culture or in suspension, for studies of cell differentiation, for research of therapeutic genes, for protein purification, etc.

Freezing chondrocytes

This invention also describes compositions and methods that are particularly effective in preserving chondrocytes, in particular in frozen form. These methods advantageously enable chondrocytes to be conserved for long periods, without affecting their functional properties. In addition, particular compositions and methods are compatible with therapeutic use and thus facilitate the preservation of chondrocytes or chondrocyte compositions intended for in vivo implantation.

Freezing can be conducted under various conditions and in the presence of various protective agents or compositions.

According to a first embodiment, freezing is performed in the presence of dimethyl sulfoxide (DMSO). DMSO is a well-known protective agent which inserts into cellular membranes and enables them to be stabilized, preventing cells from being destroyed. A typical DMSO-containing freezing medium includes, for example, 5% to 25% of DMSOs and fetal calf serum. However, to the degree that the DMSO cannot be injected in man, this type of medium is not really adapted to therapeutic use. In effect, it requires at least one treatment stage for the cells after freezing (centrifuging, rinsing, etc.) in order to eliminate the DMSO, prior to administration to a subject. This type of freezing can, nonetheless, be utilized for other uses of chondrocytes, as mentioned herein.

In a particularly advantageous embodiment, freezing is, however, performed in the absence of DMSO. More specifically, this invention presently describes methods and compositions for freezing chondrocytes under conditions which are compatible with direct therapeutic use (i.e., without treating thawed compounds). In this regard, in a preferred method of implementation, chondrocytes are conserved notably in frozen form, in a medium deprived of DMSO, comprising (human) serum albumin, a saline solution and a modified gelatin. Such a composition has been described in Application FR 2,746,109. In another preferred embodiment, freezing is achieved in a medium that comprises (human) albumin, a polysaccharide, and possibly a saline solution. The present application indeed shows that this type of medium can be used in freezing chondrocytes. The invention also describes the conditions for preparing chondrocytes, to improve their conservation. Thus, a particular object of the invention resides in a composition comprising chondrocytes, notably human chondrocytes, a saline solution, human albumin and a modified gelatin or a polysaccharide, preferably a polysaccharide. Even more preferably, such compositions comprise at least approximately $5 \times 10^6$ chondrocytes/ml. In effect, this invention shows that cells can be conserved more effectively (notably, by ensuring a better viability during thawing), when they are frozen in a concentration of at least approximately $5 \times 10^6$ chondrocytes/ml, and even more preferably of $10^7$ chondrocytes/ml, approximately, or more.

According to the invention, the preservation medium generally is prepared by intermixing the various constituents, and then adding said medium to the chondrocytes at a concentration of approximately $10^7$ cells/ml. The chondrocytes can be primary chondrocytes, freshly isolated from a biological sample, or in vitro expanded chondrocytes (for example, by monolayer cultures), or redifferentiated chondrocytes, following a three-dimensional culture (for example, in alginate beads).

To freeze chondrocytes, the saline solution employed can, more particularly, consist of a solution isotonic with plasma. The salts entering in the composition of this solution can vary. Advantageously, the composition includes chlorides, such as sodium chloride, potassium chloride, calcium chloride and/or magnesium chloride, and lactates, such as, for example, sodium lactate. In a typical example, the isotonic saline solution includes sodium chloride, potassium chloride, magnesium chloride and sodium lactate. According to another variant, magnesium chloride is replaced by calcium chloride. In this case, salt concentrations in the saline solution are equivalent or quasi-equivalent to those in a "Ringer-lactate solution". Such a solution is habitually utilized in perfusion to compensate for dehydration or a loss of physiologic liquid, for example.

According to a particular method of implementing the invention, the saline solution is composed essentially of NaCl MgCl2, KCl and lactate in the ranges of concentrations included, respectively, between 2 and 9 g/l; 0.05 and 0.2/l; 0.05 and 0.5 g/l and 0.5 to 5 g/l.

The gelatin derivatives employed in conserving chondrocytes are, more particularly, modified fluid gelatin. According to the invention, said modified fluid gelatine is typically composed of products of the hydrolysis of chemically modified collagen, which are compatible with pharmaceutical use. Preferably, it consists of products whose mean molecular weight ranges from 10 kD and 100 kD, and even more preferably, between 15 kD and 40 kD. Preferably, they are modified by reacting with an anhydride, in order to obtain a final product whose fluidity is adapted to use that is sought, for example, according to the prescriptions of patent FR 1,291,502. Preferably, this is succinic, citraconic, aconitic or maleic anhydride. A particularly advantageous modified fluid gelatine is composed of the product of the hydrolysis of collagen, with a mean molecular weight ranging between 15 kD and 40 kD, modified by reaction with succinic anhydride. According to the invention, the modified fluid gelatin can be prepared by techniques known to skilled artisan. Among the modified fluid gelatin, one may cite, by way of example, oxypolygelatine, which is obtained through polymerization of the gelatin with glyoxal and oxydation with $H_2O_2$. Other modified fluid gelatins are obtained through the reaction of the gelatine (whose molecular weight preferably ranges from around 15,000 to 36,000) with succinic, citraconic, aconitic or maleic anhydride, or succinyl or fumaryle chloride, as described in French patent n° FR 1,291,502. All of these gelatin derivatives are compatible with pharmaceutical use and can be introduced directly into the blood flow, in an isotonic saline solution. Some modified fluid gelatins have also been described in patents U.S. Pat. No. 2,525,753, U.S. Pat. No. 2,827,419 and U.S. Pat. No. 3,108,995.

The serum albumin utilized is a human serum albumin (SAH), either extracted or recombinant. The natural extracted SAH can be produced through purification, starting from biological material of human origin, through classical techniques for fractionating plasma that comes from donated blood (Cohn et al., J. Am. Chem. Soc. 68 (1946) 459 pp), or through extraction from the human placenta, according to the technique described by J. Liautaud et al.(13th International ABS Congress, Budapest; A. "Purification of Proteins. Development of biological standard", Karger (ed.), Bale, 27 (1973) 107 pp). Preferably, the purified albumin utilized within the framework of this invention is a plasmatic albumin. In particular, one may utilize a commercial plasmatic albumin solution. Recombinant SAH can be manufactured in various types of cellular hosts, preferably eucaryotic (Cf FR 2,746,109).

In conservation media, the polysaccharide utilized can vary in terms of structure and molecular weight. Preferably, it consists of a polysaccharide sulfate whose weight preferably lies between 5,000 and 500,000 daltons, even more preferably between 30,000 and 250,000 daltons. The polysaccharide can be chosen, for example, from among dextran (40,000 or 60,000 daltons), starch, hydroxyethyl (240,000 daltons), etc.

In a particular embodiment, the preservation medium is composed of plasmion (FR 2,042,381), to which human serum albumin is added, at variable concentrations.

In another, preferred, embodiment, the invention's medium is composed of Rheomacrodex$^R$, Hemodex$^R$, Plasmaclair$^R$, or Hesteril$^R$, to which the human albumin serum is added, at variable concentrations (from 5 to 45%, for a 20% albumin solution).

If necessary, the respective concentrations of different constituents can be adjusted using the following methodology:

Each of the medium constituent is distributed on multi well plates in each well at a set concentration, except for one constituent whose concentration varies. If applicable, several plates are prepared to allow simultaneous testing of the various conditions of concentration for each constituent or, if the number of wells is sufficient, these various conditions are tested on the same plate. Preferably, each condition is tested at least twice, preferably in triplicate, on the plate. A chondrocyte preparation is then introduced into each well, at a concentration on the order of $10^7$ cells/ml. The plate is placed into liquid nitrogen at $-80°$ C., (possibly following an intermediate stage in the freezer). The frozen plates are then thawed and cell viability is determined in each well, for example, by coloration with trypan blue. Each plate can be read through a robotized system, to enable numerous conditions to be treated and easily analyze the results obtained.

According to the invention, the chondrocyte composition can be conserved in frozen form, for example, at $-80°$ C., without significantly affecting the cells' functional properties. As indicated in the examples, cell viability exceeding 85% can be obtained.

Uses for chondrocyte implantation

A further object of this invention is also to utilize the chondrocytes produced by the process described above, or a composition described above, to prepare a composition intended for the implantation of chondrocytes in human beings, particularly to treat cartilaginous defects. The term "treat cartilaginous defects" designates, notably, the restoration or compensation of cartilaginous defects, which is to say particularly at least partial reconstitution of cartilage in the areas where it is defective. Preferably, this concerns utilization in an autologous context, that is, that the biological sample utilized in producing the chondrocytes comes from the subject to whom the chondrocytes that are produced will be administered.

The invention also concerns a method for restoring cartilage in vivo, including the administration, to a subject, of a composition of chondrocytes produced according to the process described in the invention, preferably composed of autologous chondrocytes.

For this purpose, the method described by the invention advantageously comprises the taking of a sample of healthy cartilage from the subject, the preparation of chondrocytes from this sample, according to the process described above, then the administration to said subject of the chondrocyte composition that is obtained in this manner.

The invention also concerns a method for treating pathologies in cartilage, comprising administration to a subject of a composition of chondrocytes produced according to the invention's process, preferably consisting of autologous chondrocytes.

Before the chondrocyte composition is implanted, it is preferable to prepare the area that is to be treated. For this purpose, the defect must be prepared to ensure that the implant will take more effectively (particularly as regards its attachment), to reduce the risks of vascularization, etc. Generally, the defect is treated in advance (in order to eliminate all defective cartilage from the area), then it is cleaned. Next, various implantation techniques can be implemented, according to the material being implanted (suspension, matrix, cartilage reconstituted in vitro).

In particular, the implantation can be performed according to the techniques described in Application WO98/08469, which involves the deposition, on the site to be treated, of a layer of collagen, in order to prevent or reduce vascularization, then, on this first layer, chondrocytes, and then, on the chondrocytes, a patch composed of semipermeable collagen.

The implantation can also be performed according to the technique described in U.S. Pat. No. 4,846,835, which consists of mechanically affixing the implant by means of a periosteal flap that is sutured to the cartilage.

In a general sense, the implant can be performed by applying various surgical techniques known to the skilled person, and which are experienced in a human clinic, notably implying a stage in which the implant is affixed during surgery, through biodegradable sutures or by the application of bioadhesives (see, for example, Minas et el., Operative Techniques in Orthopaedics 7 (1997) 323, which is incorporated into this document by reference). Examples of bioadhesives include, notably, biological glues made of fibrin and/or thrombin (FR2,448,900), or other biocompatible materials, such as Tissucol and Vieryl (see also U.S. Pat. No. 5,197,973). In this regard, this invention describes a new method for implanting chondrocytes in vivo, including affixing a biocompatible film on the area to be treated (preferably, a resorbable film (biodegradable)), which contains or is intended to receive the chondrocytes that are multiplied in vitro. More particularly, the resorbable biocompatible film is affixed onto the area to be treated, by means of a biological or biocompatible glue. In a preferred variant, the film is positioned on the cartilaginous defect, then the pocket which is thus constituted is filled with chondrocytes that are multiplied in vitro. According to the invention, this method of implantation is advantageous since it avoids recourse to periosteal sutures. In a more preferred implementation mode, the implantation is performed by applying, by means of a biological glue, a resorbable biocompatible film onto the site being treated, then a composition of chondrocytes in liquid or gel solution is introduced into the pocket formed by the film.

Thus, the invention also relates to the use of a biocompatible film, particularly a resorbable one, to prepare a composition intended for the implantation of chondrocytes into a defective cartilage. More preferably, the chondrocytes are in a liquid or gel solution, and comprise in vitro multiplied chondrocytes. More preferably, the chondrocytes are autologous chondrocytes.

The compositions and methods of the present invention can be used in treating all cartilaginous defects, notably in the femur, tibia, meniscus, ribs, etc.

Other aspects and advantages of this invention will appear while reading the examples which follow, which must be considered as illustrative, but not by way of limitation.

Specific Examples

EXAMPLE 1

Preparation of Media for the Detachment of Chondrocytes in Culture.

This example describes the preparation of new media for detaching chondrocytes in culture. These media present the advantage of detaching chondrocytes without significantly altering the cell membranes or the cells' biological properties.

Following enzymatic digestion over a 12-hour period at 37° C., rabbit cartilage was rinsed three times with a Ham F-12 medium. Then, the cells were placed into a culture, in a flask containing 15 ml of complete medium (Ham F-12, 10% SVF, 1% hepes, 1% antibiotics and 50 µl/ml of vitamin C). After confluence, the cells were transplanted with a trypsin-EDTA medium and placed into a culture in 24-well plates for 4 to 5 days. Two cellular concentrations were tested ($2.10^4$ and $5.10^4$ cells/well). Various cell detachment media were then tested, at the rate of 500 µl/well. The results obtained are presented in Table 1.

They show that the solutions tested enabled the cells to be detached from the support, thus producing isolated cells (each dissociated from the others), or groups of cells detached from the support. The results obtained show, notably, that the media specified by the invention, utilizing polyosidic derivatives, heparin in particular, in association with EDTA when applicable, enable the cells to be detached efficiently, including at low concentrations (notably, 100 UI/ml). The results obtained show, besides, that the cells thus obtained are capable of proliferating in a normal manner, after being returned to culture.

EXAMPLE 2

Production and Cryopreservation of Chondrocytes

Human joint chondrocytes are isolated from a cartilage sample, by means of mechanical then enzymatic treatment. To this effect, a biopsy taken from the operating block is placed under sterile conditions in a 50 ml tube containing a nutritive medium (HAM F12, supplemented by 50 µl/ml of gentamicin). Following verification of the absence of contamination, the biopsy is cut away with the aid of a sterile pincer and scalpel, into pieces whose dimension is less than approximately 3 $mm^3$. These pieces are then incubated in a tube, in the presence of a HAM F12 medium containing 1 mg/ml of collagenase A, either from extraction or recombinant means. The human joint chondrocytes obtained are washed several times, then are placed into a culture in a single layer for 21 days. After this period, the cells are detached in the presence of an enzymatic trypsin solution (0.005%)–EDTA (0.002%) or a heparin solution, then are washed twice in a complete culture medium. The cells which are thus detached are harvested and are delicately placed again in suspension at various concentrations, at 4° C. One portion is placed into a freezing medium including DMSO, and the other portion is placed in freezing media deprived of DMSO and of glycerol, with the following composition:

Medium 1:
  SAH at 20%: 33%
  Rheomacrodex$^R$: 67%
Medium 2:
  SAH at 20%: 33%
  Hemodex$^R$: 67%
Medium 3:
  SAH at 20%: 33%
  Plasmaclair$^R$: 67%
Medium 4:
  SAH at 20%: 33%
  Hesteril$^R$: 67%

The compositions obtained are exposed to −80° C. and then conserved in liquid nitrogen. The chondrocytes are then thawed in a double boiler at 37° C., for analysis.

Cell viability measurements were then taken at various times, by employing a vital coloration using exclusion, in the presence of blue trypan. The results obtained for freezing medium 1 (without DMSO) are presented in Table 2. They show that a very good degree of cellular viability is obtained (a viability index of up to 87%), notably once the cells are frozen at high concentrations (on the order of $10^7$ cells per ml of medium). Similar results are obtained with the 2–4 media defined above. These results show that chondrocytes can be frozen, in the absence of DMSO, with quite a high degree of viability, notably when they are frozen at a concentration of approximately $10^7$ cells per ml, or higher.

EXAMPLE 3

Analysis of the Phenotype

This example shows that chondrocytes produced according to the invention, particularly thawed chondrocytes, retain their functional properties and are capable of differentiating themselves to produce a cartilaginous extracellular matrix.

Joint chondrocytes cultivated in a monolayer loose their differentiated character during the successive passages. This process leads, notably, to progressive reduction of the synthesis of Type II collagenase, which is considered the specific marker of cartilage, and to the appearance of Type I and III collagen, which are not characteristic of this tissue. This example shows that chondrocytes which are dedifferentiated in this manner can recover their primary phenotypes when they are transferred from the monolayer culture to the three-dimensional culture (in agar rose, in alginate) or are implanted in vivo.

In order to test the potentialities of dedifferentiated chondrocytes, amplified in a monolayer and destined to be reimplanted, the expression of type II collagen was measured by RT-PCR on chondrocytes that were multiplied in vitro, frozen, thawed, then transferred in a three-dimensional culture.

3.1. Cell Cultures

To this purpose, chondrocytes that were produced and frozen according to Example 1 or 2 were thawed then transferred in alginate beads (Guo et al., Comm. Tissue Res. 19 (1989) 277). Briefly, the cells were placed in suspension in an alginate solution (1.42%) with weak viscosity, then sterilized by autoclave at a density of $1.5,10^6$ cells/ml. The suspension was then poured, drop by drop, by means of a syringe equipped with a 22-gauge needle, into a 100 mM solution of $CaCl_2$. After the beads were gelled, they were left for 10 minutes in the solution in order to complete their polymerization. They were then rinsed 3 times in the EBSS (Earl's Buffered Saline Solution), then one time in the DMEM. Finally, they were placed in DMEM+10% SVF and cultivated for 13 days at 37° C., 5% $CO_2$, with a change of medium every three days.

3.2. Extraction of the Total RNA

The beads were rinsed 3 times with PBS at 4° C., then 4 volumes of dissolution buffer (55 mM sodium citrate/EDTA 25 mM) are added on beads that are gathered at the bottom of a 50 ml tube. The suspension is incubated at 37° C. under gentle agitation, until the beads are completely dissociated (about 10 minutes). Centrifuging at 800 g for 10 minutes enables the chondrocytes to be separated from the alginate matrix. The cell pellet was subjected to extraction by guanidium isothiocyanate to obtain total RNA.

3.3. Reverse Transcription—Polymerase Chain Reaction (RT-PCR)

A reverse transcription was performed in a volume of 20 µl, containing 1 µl of oligo-d(T)$_{16}$ (20 µM), 1 µl of Rnase out (Recombinant Ribonuclease Inhibitor, 40U/µl), 4 µl of first strand 5X buffer, 1 µl of dNTPs buffer (10 mM) and 0.4 µl of reverse transcriptase (MMLV, 200 U/µl). The sample was incubated for 15 minutes at 42° C., 5 minutes at 99° C., then 5 minutes in ice. 5µl of RT product was used for the PCR in the presence of specific primers for b-actin, Type II collagen (COL2A1) and Type I collagen (COL1A1). The PCR is performed in a final volume of 20µl, in the presence of dNTPs, primers and the DNA Taq polymerase. The products of PCR were separated in 1.5% agar rose gel, in the presence of ethydium bromide, then were visualized under UV.

3.4. Results

The results obtained demonstrate the presence of the messenger RNA coding for Collagen II, after only 25 cycles of amplification. On the other hand, the RNAm of the collagen I is undetectable, even after 35 cycles of amplification. The same analysis, which was conducted on an extract originating from human dermal fibroblasts, serves as a control. Said control indicates the presence of RNAm from the collagen I, without any expression of RNAm from collagen II. These results demonstrate that the cells described by the invention exhibit a differentiated chondrocytic phenotype. Thus, these results show that the stages of in vitro culture and of freezing did not affect the cells' phenotype.

TABLE 1

Detaching chondrocytes in various media

| Cells/wells | Dissociation medium | Concentration | Treatment duration | Cell aspect |
|---|---|---|---|---|
| 2.10$^4$ | Heparin | 1000 Ul/ml (in PBS) | 20 minutes | CL |
|  |  | 500 Ul/ml (in PBS) | 15 minutes | CL |
|  |  | 100 Ul/ml (in PBS) | 15 minutes | CL |
|  | EDTA/ | 1:5000/1000 Ul/ml | 15 minutes | CL |
|  | Heparin | 1:5000/500 Ul/ml | 15 minutes | CL |
|  |  | 1:5000/100 Ul/ml | 15 minutes | CL |
|  | Heparin | 1000 Ul/ml (in PBS) | 60 minutes | CL + P |
|  |  | 500 Ul/ml (in PBS) | 60 minutes | CL + P |
|  |  | 100 Ul/ml (in PBS) | 60 minutes | CL + P |
| 5.10$^4$ | EDTA/ | 1:5000/1000 Ul/ml | 60 minutes | CL + P |
|  | Heparin | 1:5000/500 Ul/ml | 60 minutes | CL + P |
|  |  | 1:5000/100 Ul/ml | 60 minutes | CL + P |

CI: Isolated Cells (each dissociated from the others)
P: Groups (cellular layers detaching by groups)

TABLE 2

Viability of human chondrocytes following freezing in liquid nitrogen in an medium deprived of DMSO

| cartilage # | Freezing time | Cellular Concentration (cells/ml) | % surviving thawing |
|---|---|---|---|
| 8 | 24 hours | 10$^7$ | 82 |
| 13 | 24 hours | 10$^7$ | 66 |
| 13b | 24 days | 10$^7$ | 87 |
| 14 | 16 days | 1.1, 10$^6$ | 24 |

What is claimed is:

1. A method of producing a chondrocyte preparation from a biological sample, said method comprising:
    a) treating the biological sample in the presence of a recombinant enzyme capable of dissociating chondrocytes contained in said biological sample,
    b) monolayer culturing chondrocytes thus dissociated, and
    c) contacting the chondrocytes with a medium comprising at least one polyosidic derivative compound, in order to detach adhering chondrocytes.

2. The method according to claim 1, further comprising the following stages:
    d) optionally, repeating stages b) and c) once or several times, and e) recovering the cells produced.

3. The method according to claim 1, further comprising stage f) consisting of freezing the chondrocytes obtained.

4. The method according to claim 3, wherein freezing is performed in a DMSO medium.

5. The method according to claim 1, wherein the biological sample is a fragment of cartilaginous tissue or marrow, or of any other biological material comprising chondrocytes.

6. The method according to claim 5, wherein the biological sample is a fragment of cartilage.

7. The method according to claim 6, wherein the biological sample is a fragment of joint cartilage.

8. The method according to claim 6, wherein the biological sample is maintained in a culture containing a nutritive medium, either prior to or concomitant with stage a).

9. The method according to claim 1, wherein, in stage a), the biological sample is treated in the presence of a recombinant collagenase.

10. The method according to claim 9, wherein the recombinant collagenase is a recombinant bacterial collagenase or a recombinant mammalian collagenase.

11. The method according to claim 1, wherein, in stage c), the polyosidic derivative is a polyosidic polymer.

12. The method according to claim 11, wherein, in stage c), the polyosidic derivative is a polysaccharide.

13. The method according to claim 11, wherein the polyosidic derivative is selected from heparin and dextran sulfate.

14. The method according to claim 1, wherein said chondrocytes are human chondrocytes.

15. The method according to claim 14, wherein said preparation of human chondrocytes is a suspension of autologous human chondrocytes.

16. The method according to claim 14, wherein said preparation of human chondrocytes is an artificial cartilage produced in vitro.

17. The method according to claim 16, further comprising a stage in which the chondrocytes obtained are cultured on a synthetic matrix, or into a support device that has a non-adherent surface.

18. A composition comprising chondrocytes obtained by a method according to claim 1.

19. A method of producing a suspension of human chondrocytes, said method comprising:
    a) treating a cartilaginous tissue in the presence of a recombinant collagenase capable of dissociating chondrocytes contained in said tissue,
    b) monolayer culturing chondrocytes thus dissociated,
    c) contacting the chondrocytes with a medium comprising at least one polysaccharide compound, in order to detach adhering chondrocytes,
    d) optionally, repeating stages b) and c) once or several times,
    e) recovering the suspension of cells produced, and
    f) freezing the chondrocytes suspension obtained.

* * * * *